US010296927B2

(12) United States Patent
Soria et al.

(10) Patent No.: US 10,296,927 B2
(45) Date of Patent: May 21, 2019

(54) SYSTEM AND METHOD FOR PROJECTING PRODUCT MOVEMENT

(71) Applicant: IQVIA INC., Parsippany, NJ (US)

(72) Inventors: Luis Soria, Englewood, NJ (US); Sivakumar Nadarajah, Bridgewater, NJ (US)

(73) Assignee: IQVIA INC., Parsippany, NJ (US)

( * ) Notice: Subject to any disclaimer, the term of this patent is extended or adjusted under 35 U.S.C. 154(b) by 229 days.

(21) Appl. No.: 14/136,706

(22) Filed: Dec. 20, 2013

(65) Prior Publication Data

US 2015/0178745 A1 Jun. 25, 2015

(51) Int. Cl.
*G06Q 30/02* (2012.01)
*G06Q 50/22* (2018.01)

(52) U.S. Cl.
CPC ......... *G06Q 30/0202* (2013.01); *G06Q 50/22* (2013.01)

(58) Field of Classification Search
CPC .............................. G06Q 50/22; G06Q 50/24
See application file for complete search history.

(56) References Cited

U.S. PATENT DOCUMENTS

| | | | |
|---|---|---|---|
| 2005/0055275 A1* | 3/2005 | Newman et al. | 705/14 |
| 2009/0006156 A1* | 1/2009 | Hunt et al. | 705/7 |
| 2013/0073336 A1* | 3/2013 | Heath | G06Q 30/02 705/7.29 |
| 2013/0231975 A1* | 9/2013 | High et al. | 705/7.29 |
| 2014/0025429 A1* | 1/2014 | Nihal | G06F 19/327 705/7.32 |
| 2014/0143013 A1* | 5/2014 | Pavlidis et al. | 705/7.31 |

\* cited by examiner

*Primary Examiner* — Jonathan Ng
*Assistant Examiner* — Rachelle L Reichert
(74) *Attorney, Agent, or Firm* — John Maldjian; Maldjian Law Group LLC

(57) ABSTRACT

A method includes receiving data encoding search results from at least one search engine, each of the at least one search engine applying an ontology in a corresponding social-media channel, the ontology refined to account for at least one healthcare product and at least one event; retrieving a database that includes relationships between identified event and healthcare indication, the database being developed from historical sales activities of healthcare products and healthcare indications for the healthcare products; and analyzing the search results by: determining at least one event identified by the search results; comparing the at least one event with the retrieved database to determine a corresponding healthcare indication; identifying a healthcare product with the determined corresponding healthcare indication; and correlating the search results about the identified healthcare product with historical sales activities of the identified healthcare product to determine a sales trend for the identified healthcare product during a projected period.

20 Claims, 9 Drawing Sheets

FIG. 3C

| | A | B | C | D | E | F | G | H | I | J |
|---|---|---|---|---|---|---|---|---|---|---|
| 1 | File Code | PG | PG Name | Mfr # | Status | CMF | Product Description | Mfr Name | Dollars | USC |
| 2 | 4 | 00000006 | ***** KIT | 24124 | | 1256403002 | ********** TAB FC,25MG, X4 C-4,25-34 (DD)(RX) | AMGEN INC | $1,181.72 | 09130 |
| 3 | 4 | 00000006 | ***** KIT | 24124 | | 1256403002 | ********** TAB FC,25MG, 0425-4' (DD) | AMGEN INC | $259.43 | 09130 |
| 4 | 4 | 00000007 | ***** 50MG PFS | 24124 | | 1256403010 | PRF 50MG; 098MLX-X1 0435-J4 (DD)(RX) | AMGEN INC | $2,363.44 | 09130 |
| 5 | 4 | 00000007 | ***** 50MG PFS | 24124 | | 1256403012 | ********** PRF 50MG; 098MLX- 0435-01 (DD)(RX) | AMGEN INC | $590.86 | 09130 |
| 6 | 4 | 00000008 | ***** ***** 50 MG | 24124 | | 1256403012 | ********** PRF 50MG; ML,0 98MK4 0445-04 (DD)(RX) | AMGEN INC | $2,363.44 | 09130 |
| 7 | 4 | 00000008 | ***** 50 MG | 24124 | | 1256403013 | ********** PRF 50MG; ML,0 98MK4 0445-01 (DD) | AMGEN INC | $259.86 | 09130 |
| 8 | 4 | 00000009 | ***** 25MG/0.5ML PFS | 24124 | | 1256403014 | ********** PRF 50MG; ML,0 98MK4 0445-01 (DD) | AMGEN INC | $259.86 | 09130 |
| 9 | 4 | 00000009 | ***** 25MG/0.5ML PFS | 24124 | | 1256403015 | ********** PRF 50MG; ML,0 98MK4 0445-01 (DD) | AMGEN INC | $259.86 | 09130 |
| 10 | 4 | 00000010 | REMICADE | 09057 | | 1580154001 | REMICADE VIAL DRY 50.06 MG, 1 0030-41 (DD)(RX) | AMGEN INC | $259.86 | 09130 |
| 11 | 4 | 00000018 | ARAVA LEFLUNOMCE | 26844 | | 1057515001 | ARAVA,TAB FC,10MG,50 2360.50 (DD)(RX) | SANOFI AVENTIS P*R | $858.42 | 09140 |
| 12 | 4 | 00000018 | ARAVA LEFLUNOMCE | 26844 | | 1057515003 | ARAVA,TAB FC,20MG,50 2361.50 (DD)(RX) | SANOFI AVENTIS P*R | $858.42 | 09140 |
| 13 | 4 | 00000018 | ARAVA LEFLUNOMCE | 26844 | | 1057515005 | ARAVA,TAB FC, 100MG, ***** 2162.05 (RX) | SANOFI AVENTIS P*R | $508.12 | 09140 |
| 14 | 4 | 00000018 | ARAVA LEFLUNOMCE | 26534 | IH | 1377015001 | LEFLUOMI CE,TAB FC,20MG,50 0160.50 (DD)(RX) | PRASCO LABS | $54.18 | 09140 |
| 15 | 4 | 00000018 | ARAVA LEFLUNOMCE | 26534 | | 1377015001 | LEFLUOMI CE,TAB FC,20MG,50 0161.50 (RX) | PRASCO LABS | $54.29 | 09140 |
| 16 | 4 | 00000018 | ARAVA LEFLUNOMCE | 25490 | IH | 1377012002 | LEFLUOMI CE,TAB 20MG,50 2559.00 (RX) | PHYS TOTAL CARE | $95.65 | 09140 |
| 17 | 4 | 00000018 | ARAVA LEFLUNOMCE | 25490 | IH | 1377012002 | LEFLUOMI CE,TAB 10MG,50 6170.00 (RX) | PHYS TOTAL CARE | $45.99 | 09140 |
| 18 | 4 | 00000018 | ARAVA LEFLUNOMCE | 28857 | TH | 1377014001 | LEFLUOMI CE,TAB 20MG,50 0552.01 (DD)(RX) | TEVA PHARMACEUTICALS | $45.32 | 09140 |
| 19 | 4 | 00000018 | ARAVA LEFLUNOMCE | 28857 | TH | 1377014012 | LEFLUOMI CE,TAB 10MG,50 0551.01 (DD)(RX) | TEVA PHARMACEUTICALS | $44.26 | 09140 |
| 20 | 4 | 00000018 | ARAVA LEFLUNOMCE | 00055 | | 1377015001 | LEFLUOMI CE,TAB FC,20MG,50 3056.61 (DD)(RX) | SANDOZ | $24.92 | 09140 |
| 21 | 4 | 00000018 | ARAVA LEFLUNOMCE | 00055 | | 1377015012 | LEFLUOMI CE,TAB FC,20MG,50 5057.51 (DD)(RX) | SANDOZ | $23.00 | 09140 |
| 22 | 4 | 00000018 | ARAVA LEFLUNOMCE | 28857 | | 1377016001 | LEFLUOMI CE,TAB FC,20MG,50 0173.56 (DD)(RX) | TEVA PHARMACEUTICALS | $22.68 | 09140 |
| 23 | 4 | 00000018 | ARAVA LEFLUNOMCE | 28857 | | 1377016012 | LEFLUOMI CE,TAB 10MG,50 0174.56 (DD)(RX) | TEVA PHARMACEUTICALS | $25.16 | 09140 |
| 24 | 4 | 00000018 | ARAVA LEFLUNOMCE | 09341 | IH | 1577017001 | LEFLUOMI CE,TAB 10MG,500 0488-05 (RX) | PAR PHARM | $1,050.58 | 09140 |

SYSTEM AND METHOD FOR PROJECTING PRODUCT MOVEMENT

BACKGROUND

The advent of the Internet, social media and mobile applications ("apps") has provided a new venue for healthcare product manufacturers to harvest information regarding their healthcare products.

OVERVIEW

In one aspect, some implementations provide a computer-implemented method for projecting future sales activities for at least one healthcare product, the method including: receiving data encoding search results from at least one search engine, each of the at least one search engine having applied an ontology to text mine in a corresponding social-media channel, the ontology refined to account for at least one healthcare product and at least one event; retrieving a database that includes historical events related to healthcare indications, the database being developed from historical sales activities of healthcare products and healthcare indications for the healthcare products; and analyzing the search results by: determining at least one event identified by the search results; comparing the at least one event with the retrieved database to determine a corresponding healthcare indication; identifying a healthcare product with the determined corresponding healthcare indication; and correlating the search results about the identified healthcare product with historical sales activities of the identified healthcare product to determine a sales trend for the identified healthcare product during a projected period.

Implementations may include the following features. In some implementations analyzing may further include: determining a statistical correlation between the search results about the identified healthcare product with historical sales activities of the identified healthcare product. Determining the statistical correlation may further include: performing a regression analysis on the historical sales activities to determine the sales trend for the identified healthcare product, the regression analysis accounting for contributions from the at least one event as identified from the search results.

Some implementations may further include comparing the determined sales trend for the identified healthcare product with actual sales data during the projected period. Some implementations may additionally include: identifying a difference between the determined sales trend and the actual sales data during the projected period; and refining the correlation between the search results about the identified healthcare product and the historical sales activities of the identified healthcare product such that the identified difference is reduced.

Some implementations may further include presenting the determined sales trend in a graphic user interface. Some implementations may further include: providing the determined sales trend to cumulatively build a profile of the identified healthcare product. Some implementations may additionally include: recording actual sales data for the identified healthcare product in the profile; and comparing the sales trend for the identified healthcare product in the profile to actual sales data.

Some implementations may further include: receiving the ontology for the at least one healthcare product; refining the ontology by incorporating reporting parameters that include at least one of: product level data, supplier data, facility level data, or class of trade data.

Some implementations may further include: receiving the ontology for the at least one healthcare product; refining the ontology by incorporating event-driven parameters relating to at least one of: a natural event, or a government event.

In another aspect, some implementations may include a computer system computer system, comprising at least one processor, wherein the at least one processor is configured to perform the operations of: receiving data encoding search results from at least one search engine, each of the at least one search engine having applied an ontology to text mine in a corresponding social-media channel, the ontology refined to account for at least one healthcare product and at least one event; retrieving a database that includes identified events related to healthcare indications, the database being developed from historical sales activities of healthcare products and healthcare indications for the healthcare products; and analyzing the search results by: determining at least one event identified by the search results; comparing the at least one event with the retrieved database to determine a corresponding healthcare indication; identifying a healthcare product with the determined corresponding healthcare indication; and correlating the search results about the identified healthcare product with historical sales activities of the identified healthcare product to determine a sales trend for the identified healthcare product during a projected period.

Implementations may include the following features. Analyzing may further include: determine a statistical correlation between the search results about the identified healthcare product with historical sales activities of the identified healthcare product. Determining the statistical correlation may further include: performing a regression analysis on the historical sales activities to determine the sales trend for the identified healthcare product, the regression analysis accounting for contributions from the at least one event as identified from the search results.

Implementations may further include: comparing the determined sales trend for the identified healthcare product with actual sales data during the projected period. The operations may further include: identifying a difference between the determined sales trend and the actual sales data during the projected period; and refining the correlation between the search results about the identified healthcare product and the historical sales activities of the identified healthcare product such that the identified difference is reduced.

The operations may further include: presenting the determined sales trend in a graphic user interface. The operations may further include: providing the determined sales trend to cumulatively build a profile of the identified healthcare product.

The operations may further include: receiving the ontology for the at least one healthcare product; and refining the ontology by incorporating reporting parameters that include at least one of: product level data, supplier data, facility level data, or class of trade data.

The operations may further include: receiving the ontology for the at least one healthcare product; and refining the ontology by incorporating event-driven parameters relating to at least one of: a natural event, or a government event.

Implementations of the above techniques include a method, computer program product and a system. The computer program product is suitably embodied in a non-transitory machine-readable medium and includes instructions executable by one or more processors. The instructions are configured to cause the one or more processors to perform the above described actions.

The system includes one or more processors and instructions embedded in a non-transitory machine-readable medium that are executable by the one or more processors. The instructions, when executed, are configured to cause the one or more processors to perform the above described actions. The default position is not to use any external databases, but the system could be configured to perform a database check if needed.

In yet another aspect, some implementations provide a computer-readable medium comprising software instructions that, when executed by a computer, causes the computer to perform the operations of: receiving data encoding search results from at least one search engine, each of the at least one search engine applying an ontology in a corresponding social-media channel, the ontology refined to account for at least one healthcare product and at least one event; retrieving a database that includes identifiable events related to healthcare indication, the database being developed from historical sales activities of healthcare products and healthcare indications for the healthcare products; and analyzing the search results by: determining at least one event identified by the search results; comparing the at least one event with the retrieved database to determine a corresponding healthcare indication; identifying a healthcare product with the determined corresponding healthcare indication; and correlating the search results about the identified healthcare product with historical sales activities of the identified healthcare product to determine a sales trend for the identified healthcare product during a projected period.

The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

FIG. 3C is yet another screen shot showing search criteria established according to some implementations.

DETAILED DESCRIPTION

Figure 1A:
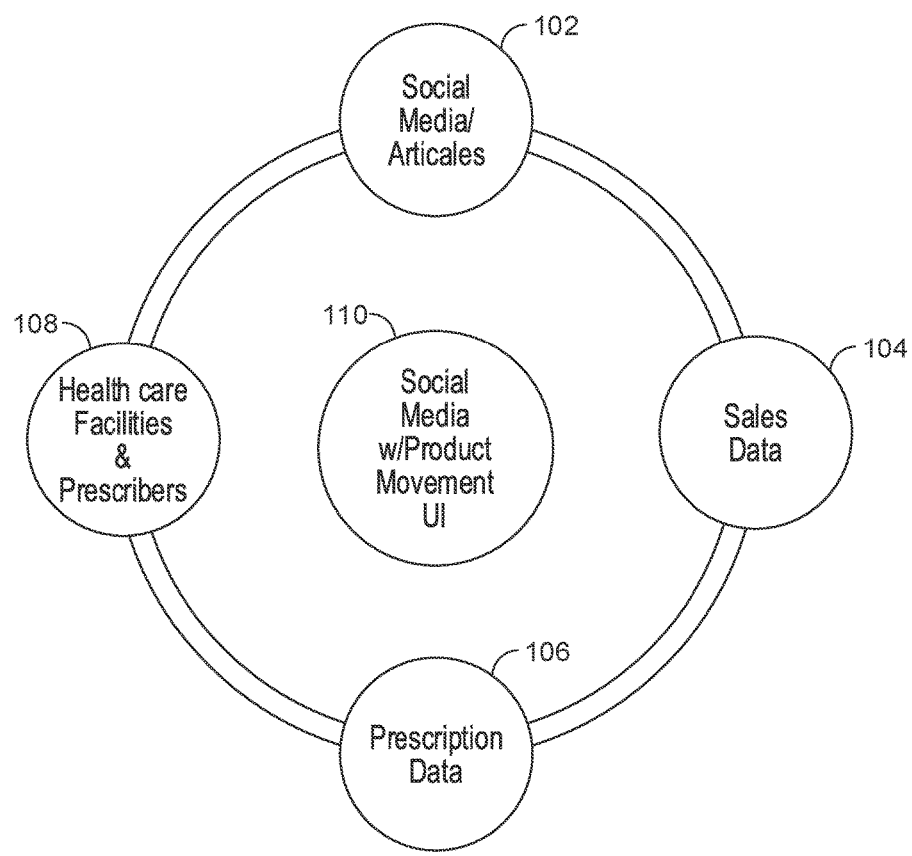
FIG. 1A is a diagram illustrating a high level relational view of a tool of utilizing social media to project product movement.

This disclosure generally describes a system and method for projecting future sales or prescription data based on search results from postings at on-line communities (such as social networking web-sites) and a database showing relationships between identified events and healthcare indications. By comparing the search results against historical sales and prescription data, some implementations provide clients with real-time or near real-time projection and forecast (by data feed, UI, or consultancy) of product movement. Thus, incorporating a social media into prescription data reporting gives users insight into why product movement occurs, such as from changes in consumer perception, or the occurrence of a manmade or natural event (e.g., a disaster or change in healthcare policy).

Generally speaking, based on the reporting of sales prescription data, the pharmaceutical industry (and medical device industry) lacks the ability to explain why sales movement of a particular healthcare product occurs and whether there are real-time events transpiring that may affect future performance. Global and/or regional events, and consumer perception, for example, can affect need or availability performance between normal reporting cycles. The interwoven effect of global/regional events and consumer perception may leave the pharmaceutical industry (and medical device industry) ill prepared to respond to changes in product trends. Failure to account for social behavior in reporting, may lead to inaccurate and often misleading perceptions of market trends. Additionally, the lack of single source coupling of sales/prescription data to social behavior reported by online media may lead to inadequate consistency, complicating the interpretation of cause and effect.

Providing customers with a single source projection/forecast of product movement tied to social media rationale can resolve the above failures and may distinguish a product offering over the competition. As illustrated by the high level relational view of FIG. 1A, some implementations disclosed herein may provide a social media with product movement user interface (UI) 110. UI 110 may enable clients to obtain, or consultants to relay, opportunities that become available during global or regional events.

In some implementations, UI 110 is configured to analyze, not only sales data 104, prescription data 106, but also social media and articles 102. For example, social and online media channels are searched based on ontologies and semantic filters built from raw and reporting sales/prescription data parameters as well as event driving parameters, such as healthcare policy discussions and disaster related terms. To search online media channels, a feed reader may track one or more on-line communities. The tracking can be done in real-time through a feed reader as the comments are posted. The tracking can also be done in a batch after the on-line postings have reached a certain size or on an hourly or daily basis.

The postings may be scanned based on a healthcare taxonomy and a set of linguistic rules, both included in the ontology. The taxonomy may also include custom components specific to a healthcare product or a medical condition. A healthcare product may generally include any substantive or service related to health care. Example healthcare products may include but are not limited to prescription pharmaceuticals, over-the-counter (OTC) drugs or devices, alternative medicine products or treatments, dietary supplements, cosmetics, etc.

Search results are weighted, calibrated based on historical sales and prescription data, and presented to the user as direct data feed or via UI 110 for consultant interaction.

The identified opportunities, as illustrated by FIG. 1A, may provide clients with a more agile and reliable distribution strategies to respond to changing product trends. The level of information revealed can also provide unique insight to data management and client service by proactively spotting, explaining, or communicating forthcoming data fluctuations for users not yet purchasing a new product offering. Moreover, consultation efforts may be elicited for those clients viewing the social media with integrated historical data application user interface, as disclosed herein.

Figure 1B:
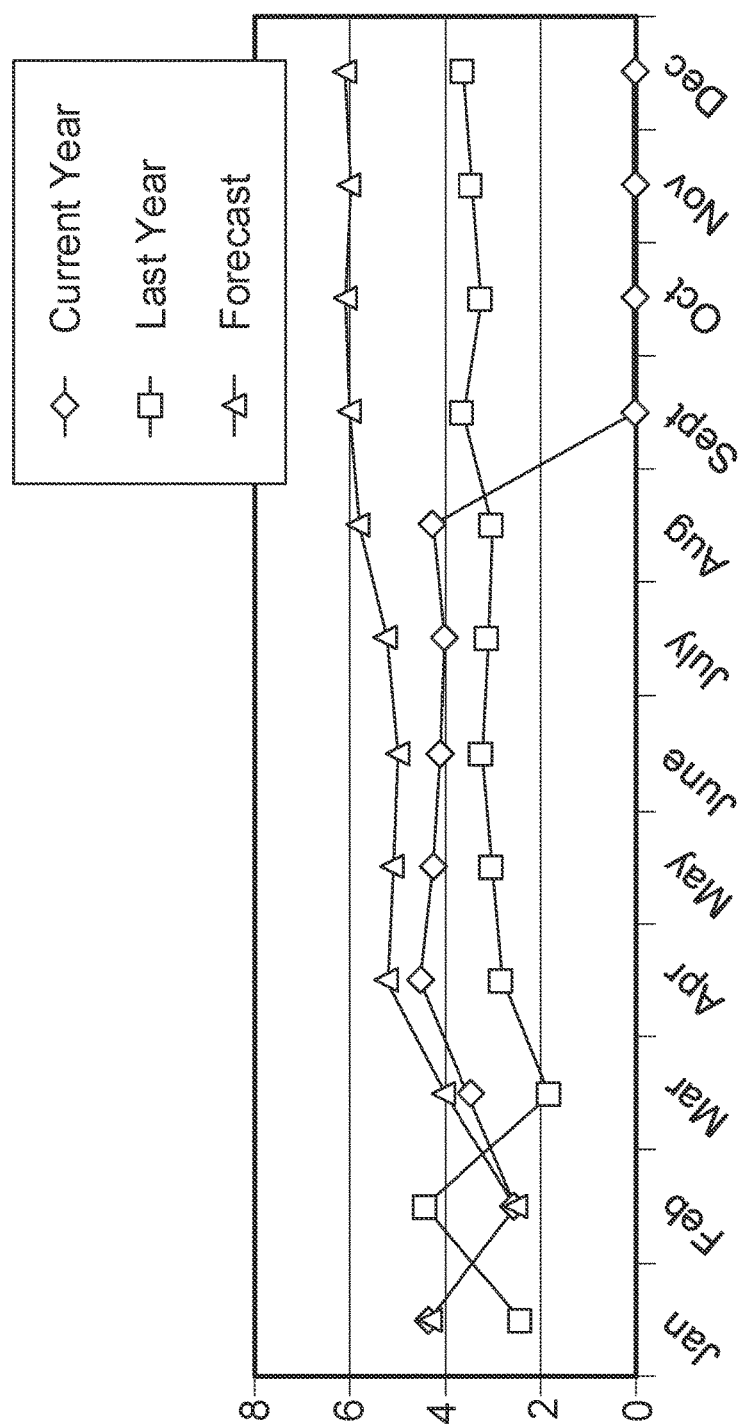
FIG. 1B shows forecasting future sales by identifying trending data in current sales based on events and historical data.

FIG. 1B shows forecasting future sales by identifying trending data in current sales based on events and historical data. In the mock example as illustrated, current year is 2013, last year is 2012, forecast curve represent sales data, as predicted in part based on last year's data before the actual sales data were logged. In one example, the predicted sales data may be driven in part by events impacting health care prescription and sales. In one example, if drug prohibition were to take effect August 2013 which means group purchasing organizations (GPOs) will be unable to negotiate on public health service (PHS) pricing for out-patient services, an increase in prescription drug purchases via the retail channel may be expected to ensue in the subsequent months. As illustrated, both the actual data for the current year and the forecast year demonstrated an increase in sales at out-patient facilities from March to August. No current data was available after August.

Existing data solutions to customers fail to project product movement based on sales/prescription data and global or region events captured via social and online media. In contrast, some implementations as disclosed herein analyze sales/prescription data reporting feeds against real-time global/regional events reported on social and online media channels to provide real time product movement projections and insight as to why certain movement occurs.

Figure 2A:
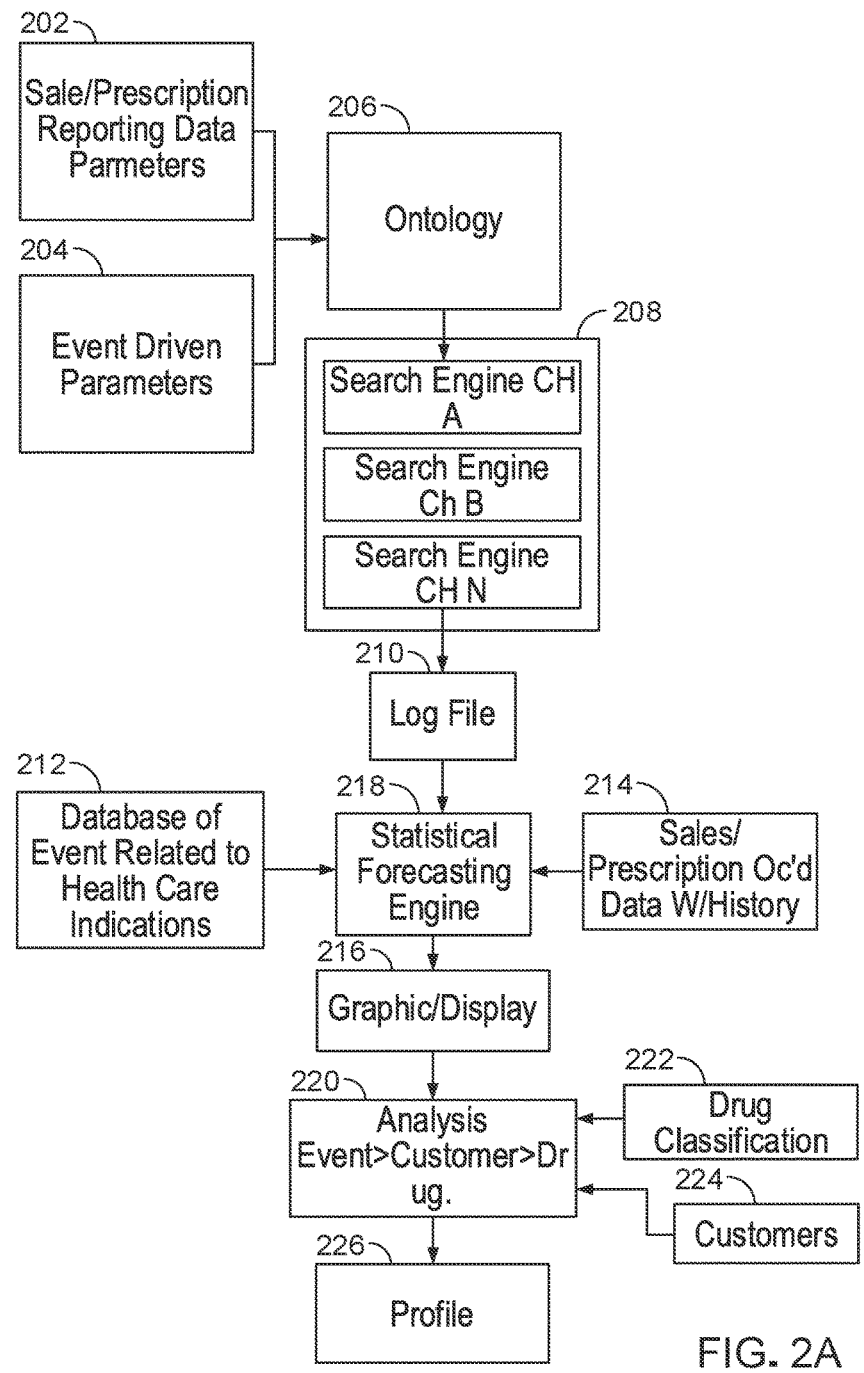
FIG. 2A is a diagram illustrating a process flow according to some implementations to generate a forecast profile by analyzing a database of events related to health indications and current events as revealed from text mining social media channels.

FIG. 2A is a diagram illustrating a process flow according to some implementations to generate a forecast profile by analyzing a database of events related to health indications and current events as well as search results identified from text mining social media channels. In some implementations, social media channels are searched based on ontologies and semantic filters built from raw and sales/prescription reporting data parameters as well as event driven parameters, such as healthcare policy discussions and event related terms. Search results are weighted, calibrated based on historical sales and prescription data, profiled, and presented to the user as direct data feed or via a user interface for consultant interaction.

As illustrated in FIG. 2A, text mining may be performed by each search engine to comb through the corresponding social media channel. In particular, text mining may triage postings from each social media channel according to ontology 206.

Ontology 206 may sometimes be known as a taxonomy. The taxonomy may be laid out in a resource description framework (RDF) language. A SPARQL Protocol and RDF Query Language (SPARQL) may be used to retrieve or manipulate data stored in the RDF format. In addition to RDF, the definitions of classes, properties and the relationships (sometimes referred to as the schemas) between the classes or properties, may also be specified according to a web ontology language (OWL).

Generally, ontology 206 may include healthcare taxonomy incorporating standard libraries such as the Medical Subject Headings (MeSH) as provided by the National Library of Medicine. The healthcare taxonomy may help identifying healthcare conditions in need for a particular healthcare product. Additional parameters can be later incorporated to account for previously unforeseen rationale.

In particular, ontology 206 may be derived from sales and prescription reporting data parameters 202. Sales and prescription reporting data parameters 202 may include items related to a drug, such as, for example, wholesale brand names or generics names, manufacturer names, etc. The names can include full names, abbreviated names, acronyms, nationally recognized names, regionally used names, nicknames, chemical formulas, etc. In the context of a particular drug or medical device product, sales and prescription reporting parameters 202 may also include product level (e.g., dosage level for each pill, clearance duration for each dose, size parameters of a disposable medical device, expiration parameters for each implantable device, etc.), data supplier names (including software vendors providing the reporting software), facility level names (i.e. retail store chains, hospitals, clinics, mail orders and the like, in the distribution of a healthcare product or healthcare products of a manufacturer), classes of trade (i.e., how pricing data is reported to government agencies), etc. In other words, sales and prescription data 202 may fine tune ontology towards a particular healthcare product or manufacturer by supplying the specially tailored sales and prescription reporting data parameters 202.

Ontology data 206 may also be derived from event driven parameter 204. These event driven parameters may signal a global or region event with implications on the demand for a particular healthcare product, for example, a drug or a medical device. Event driven parameters may be based on, for example, a human event impacting healthcare policy. Examples may include healthcare and welfare related policy debate in the legislature, in a judicial proceeding, or in general forum that can change public opinion. Example legislature may include both the state level and the federal level. Example judicial proceedings may include a proceeding, in any form, at any stage, in a state or federal judicial forum. Examples government events may also include notices issued by and comments received by regulating government agencies, such as the department of health and human services (DHHS). Generally, these notices and comments are related to the administration of a particular healthcare or welfare law. The administration of a healthcare law generally corresponds to the implementation of an enacted law. The detailed implementation may give rise to more discussions on social media as the regulations and rules are promulgated to affect the daily life of people from all walks of life.

In one example, as legislators propose bills affecting reimbursement of healthcare products, as these bills are debated, as the bills are passed and enacted into law, and as the rules are promulgated by the legislature, the impacted healthcare product may experience price and demand changes in a managed care market. Particularly, the likelihood of passage of these bills may be sensed from social media channels, and the impact of these bills may be correlated with historically comparable bills passed and enacted in a similar context.

Event driven parameters may be based on, for example, a natural event with healthcare implications. In another example, an outbreak of flu may lead to more demand for vaccines, an earth quake may give rise to more demand for water-treatment healthcare product etc., in the months directly ensuing the outbreak. Such outbreaks may be sensed in social media channels and the likely impact of such events may be gauged based on the responses gauged from social media channels.

Generally, event driven parameter 204 may include an associated temporal parameter. In other words, event driven parameters 204 may be time-sensitive. For example, in the healthcare policy example, discussions immediately preceding floor debates at legislatures may be more paramount than discussions after these floor debates. By contrast, in the natural event example, discussions immediately following the outbreak of the bird flu may be more meaningful than discussions preceding the outbreak (or long after the outbreak). In some cases, discussions around anniversary dates of a past event may be more relevant than discussions at other times. For example, psychiatry drugs for depression and anxiety may experience more fluctuations in demand around the anniversary dates o, for example, the Columbine shooting, the Sandy Hook shooting, the Boston Marathon bombing, the 9'11 attack, etc.

Event driven parameter 204 may also include an associated regional parameter. In other words, event driven parameters 204 may be location-dependent. For example, in the healthcare policy example, discussions immediately preceding floor debates in a state legislature may be more relevant to price or demand fluctuations in that state. These floor debate may also be relevant to price or demand fluctuations in the neighboring states, for example, if drug prohibition for a healthcare product is passed in one state, demand for the healthcare product may be impacted in the surrounding neighboring state.

In addition to the taxonomy prescribing the vocabulary, ontology 206 may also include a set of linguistic rules. The set of linguistic rules may include logic operations for conducting text searches as well as quantitative indices for numerical weights for each hit. The logic operations may include Boolean search operators for text strings, such as, for example, disjunctive (OR), conjunctive (AND), and exclusive (NOT), etc. The logic operations may also include any combination of the simple logic operations nested by, for example, quotation marks (including single quotes and double quotes), parenthesis, brackets, etc. The logic operations may further include textual string operations, such as concatenation, transposition, substitution, appending operations, etc. The logic operations may further include embedding wildcard criteria anywhere in a textual string. The logic operations may additionally include nexus criteria of search terms, for example, whether the terms sought after may be found next to each other, in the same sentence, within a number of letters, characters, words, or sentences, within the same paragraph, within the same posting/comment, within a number of postings, etc.

The set of linguistic rules may also include rules for matching term, phrases, patterns, etc. For example, the set of linguistic rules may assign a weight for each matching term, each matching phrase, and each matching pattern. The specified term, phrase, sentence, as well as the assigned weight may be adjustable. The specified term, phrase, or sentence may be considered in determining whether a particular on-line posting is noteworthy. The manner in which the specified term, phrase, and sentences are considered in the determination may be adjustable as well.

Specifically, words defined in the ontology may be assigned corresponding weights. If a defined word has been identified in a particular posting, the weight corresponding to the defined word may be directed to a numerical score of the posting. The scoring may be cumulative. For example, if a defined word has occurred in a posting multiple times, the numerical score of the posting may include the corresponding weight of the matching term multiplied by the number of occurrence. In some implementations, however, the score accumulation may not be linear. In one configuration, the weight may be tapering off for later occurrences. In another configuration, the weight may be increasing for later occurrences. In yet another configuration, the weight may be initially increasing and then tapering off after a number of occurrences. The transition number may be adjustable, depending on the context.

The linguistic rules may be targeted at a particular event-driven parameter, such as, for example, flu outbreak. The linguistic rules may be targeted at a combination of event-driven parameters, such as, for example, flu outbreak and allergy season, etc. The linguistic rules may be tailored to look for cross-correlation between a healthcare product and an event-driven parameter. The linguistic rules may also be developed for one manufacturer of healthcare product or a group of healthcare products.

Generally, the linguistic rules may include the assigned weight for each matching pattern. For example, if the matching terms occur within the same sentence, the assigned weight may be higher than if the matching terms occur with less proximity (for example, within the same paragraph, etc.). In some configurations, a proximity-dependent weighting may assign more weight to a posting if the matching terms are separated by fewer words. For example, the posting may receive more weight if the matching terms occur within five words than if the matching terms occur within ten words. In contrast, some configurations may favor postings with words more separated. In still other configurations, the proximity factor may not be monotonic. For example, the weight assigned to the posting may be maxed out for a certain range of word separations. Outside the range, either smaller or larger, the weight assigned to the posting may be reduced. The optimal range may be adjusted depending on the context of the discussion.

Moreover, the linguistic rule may include an additional weight to indicate how likely the postings may be relevant to an identifiable event, for example, a flu outbreak. In some implementations, the linguistic rules may factor in the relevancy of the forum where the postings come from. Similarly, if the postings quote postings directed at the on-line discussion forum for a particular event or the aftermath of the particular event, then the quoted link may cause additional relevancy weight to be allocated to the postings. Example event can include disaster type event, political or legislative development, etc. In some configurations, if the postings cite an established or authoritative source, such as published articles or surveys regarding the identifiable event or the aftermath, the postings may also receive the additional relevancy score. Published articles or surveys may not be limited to scientific or academic journals etc. Instead, published articles or surveys may include any media, such as, for example, NYTimes on-line, Wall Street Journal on-line, etc.

Numerical weighting may quantify each identified posting so that the identified postings can be ranked. Generally, on-lines users of an on-line resource may number in tens of millions. In some implementations, the weights of each identified postings may be aggregated for each discussion thread in which the postings belong. The aggregated weight may lead to a more comprehensive ranking. For example, a legislative development relating to a healthcare policy change at the federal level may impact everyone in the country. Yet, depending on the context, the legislative development may not be discussed in as many comments as a terrorist attack, such as the Boston Marathon bombing. In other words, the legislative development related to a healthcare policy change may not be as heavily reported as the Boston Marathon bombing, as the events unfold. But the legislative development can affect more people than the Boston Marathon bombing, if the healthcare policy were to take effect.

The numerical weight may yield a score and the score may be compared against a threshold. The threshold may function as a cut-off level to weed out postings less likely to impact on the sales of a healthcare product. In some implementations, the threshold comparison may be a multi-dimensional comparison so that the importance of each identified posting may be gauged in more than one dimension. Candidate dimensions may include, for example, the space proximity of keywords identified in each posting or a particular discussion thread, the context of the discussion thread, the specificity of references to a particular healthcare benefit or adverse effect of a particular healthcare product, the degree of the relevancy to the healthcare product, etc. A multi-dimensional comparison may factor in multiple considerations as a refinement over comparing with one cut-off level. However, a multi-dimensional comparison may be more computation intensive and hence may incur more latency. Some implementations, however, may include a mechanism to hop between a single-factor comparison and a multi-factor comparison, depending on, for example, a computing load on a particular server allocated to the search. Other implementations may allow the comparison to be refined from a single-factor to multiple factors when, for example, the relevancy degree falls below a border line but remains above a baseline threshold for being relevant. Hence, the comparison, as well as the computation, may be adapted for a particular scenario in the semantics analysis.

Historically, linguistic processing is regarded as soft science for lack of formal logic when compared to other disciplines such as physical sciences disciplines. In a sense, problems in identifying an impact of a global/regional event on the sale of a particular healthcare product may be more likely addressed by empirical evidence rather than formal logic. Instead, fuzzy logic approaches find plentiful applications in this context. As computing machines may be inherently better suited to perform strictly formal logic and arithmetic operations, a machine implementation for semantics analysis may attempt to mimic a fuzzy logic approach by building on a combination of formal logic and arithmetic blocks. The combination may be adapted for particular scenarios encountered in the semantics analysis.

Based on the ontology as well as the linguistic rules, text mining may be performed to extract search results from an ocean of information presented in the social media channels 208, as discussed above. Search results may be received from the search engines for each corresponding social-media channel A through N, as illustrated in Fig. The received search results may be consolidated in a log file 210. For example, received search results may be consolidated and then weighted to gain an actionable observation by weight/consensus. In the log file, search results may be bucketed with corresponding weights. In some implementations, buckets characterize identifiable events (natural disaster, legislative development, opinion polls, etc.) into different bins with corresponding weights. The weights may be determined by the aggregated weight after consolidating search results from all social media channels.

Figure 2B:
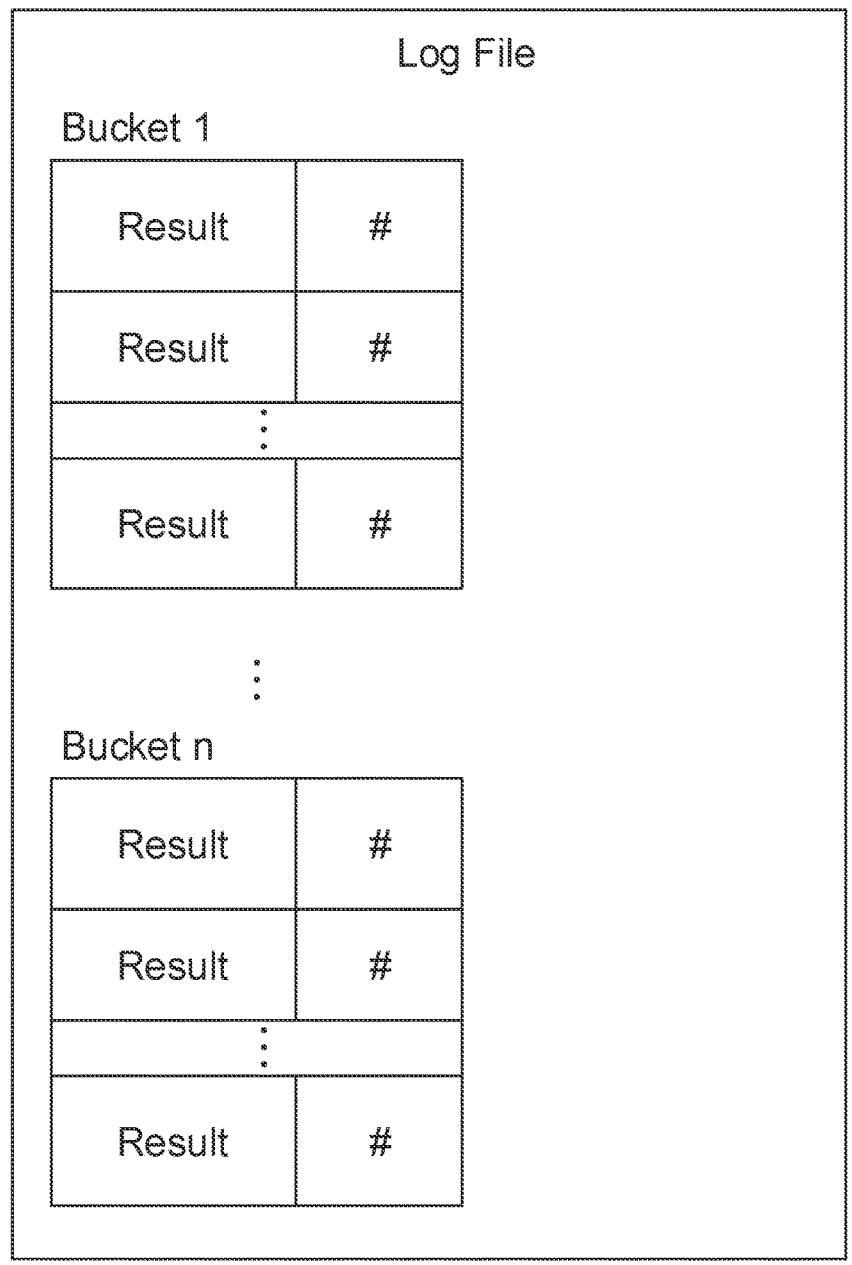
FIG. 2B illustrates an example log file as generated according to some implementations.

FIG. 2B illustrates an example log file as generated according to some implementations. As shown in FIG. 2B, a log file may include several buckets and each bucket may include several pairs of search result and the associated weight. A particular weight may be generated in accordance with the scoring procedure described above. The particular weight may be used to determine, for example, the degree of relevancy to an identifiable event with implications of a healthcare indication, causally linked to, for example, a healthcare product. Weights at search results may be assigned based on several criteria, such as, for example, by source, activity level, and impact.

Source may refer to the author of the information on social media channels. For example, source information may come from on-line postings by physician, consumers, event participants, or event spectators. In some implementations social media and other online content, such as blogs, twitter, linkedIn, facebook, online forums, and news channels, may be searched in real-time relative to the above identified parameters. Multiple search engines delegated to specific channels may be used to extract matching occurrences.

Figure 2C:
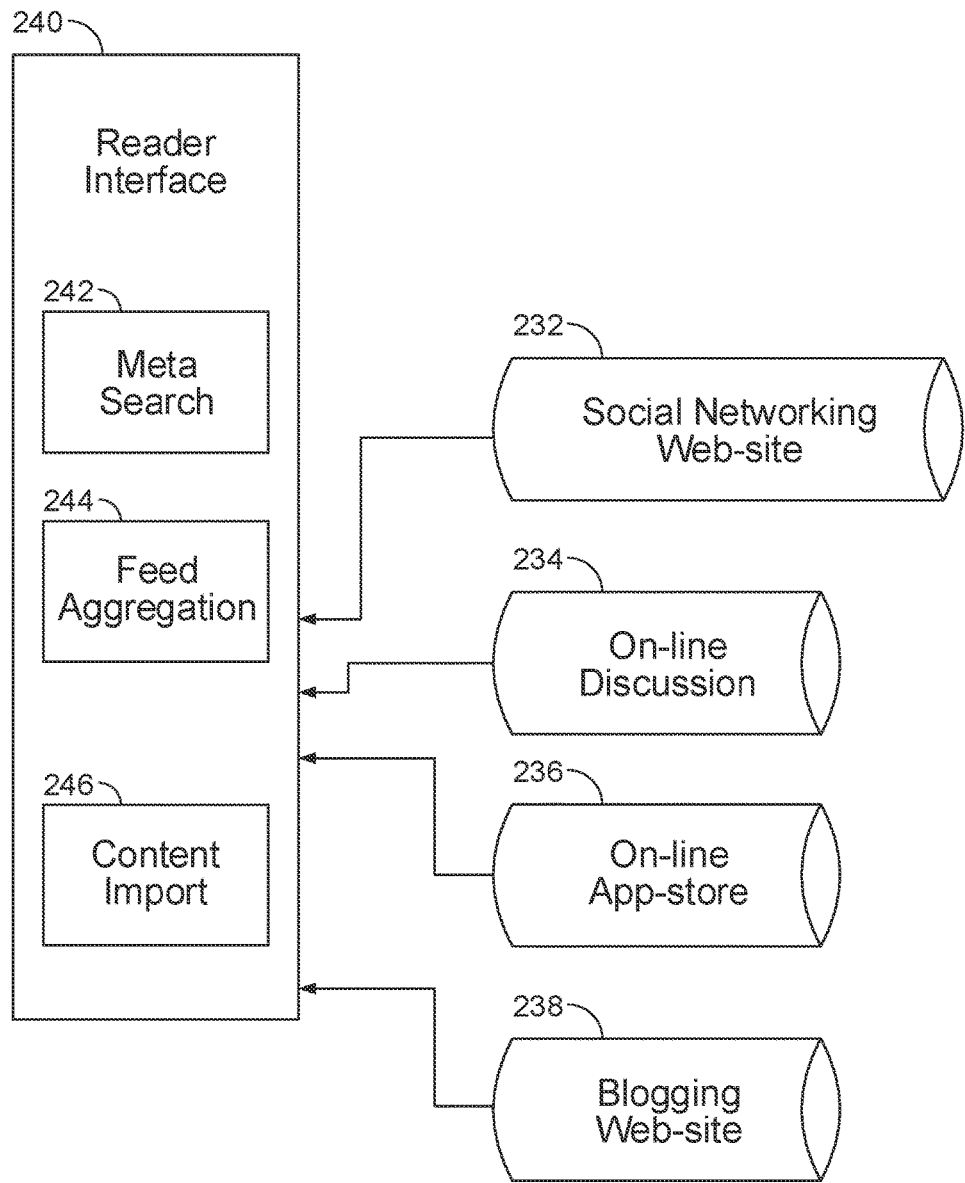
FIG. 2C shows an example feed reader used in some implementations.

Referring to FIG. 2C, users may post comments on a social networking web-site 232. Such postings may be related to a healthcare product. For example, a Facebook user may post daily observations when consuming a healthcare product. Such observations may include any subjective or objective changes as discussed above. The postings can include information pertaining to potential adverse effects of a healthcare product. If harvested and complied, such information may be highly valuable to a healthcare product manufacturer. Facebook is just one example of a social networking web-site. Other social networking web-sites may include Twitter, MySpace, Google+, etc.

Moreover, users may discuss a healthcare product at an on-line discussion forum 234. The on-line discussion forum may be an on-line portal sponsored by the manufacturer of the healthcare product. User registration may be required in order to for a user to access the on-line portal. As such, a posting may be linked to a registered user. At the discussion forum, a registered user may be able post questions when the registered user is considering a particular healthcare product.

Responses may come from fellow consumers, who may have used the particular healthcare product. Fellow consumers may attest to using the healthcare product based on their own experiences. Fellow consumers may also reveal caveats of using the healthcare product, which may not be officially published. Fellow consumers could also advise against using the healthcare product if they had encountered negative results while using the healthcare product. Fellow consumers may also advise against taking the product under certain circumstances such as certain times of day, in combination with certain foods, and/or in association with other medicines. Sometimes, fellow consumers could refer to what they heard from other consumers or earlier postings by someone else.

Responses may also come from healthcare professionals, including, for example, physicians and medical researchers. Healthcare professionals may expressly endorse a healthcare product with affirmative opinions. Healthcare professionals may also express outright dismissal about a healthcare product based on their own research or experience. Healthcare professional may also express a mixed view about the healthcare product, for example, qualified endorsement or dismissal under certain circumstances.

Postings may also come from event participants or event spectators, such as, for example, those who participated in the Boston Marathon or those who witness the bombing during the marathon. The participants may be relatively smaller in number compared to the witnesses. But, some witnesses may have experienced the bombing with closer proximity and may be better positioned to account for the incident, or more likely to be impacted by the incident to be in need of a healthcare product.

As discussed above, the contents of such discussions may contain valuable information. However, combing through seas of such information to identify global or regional event with noticeable impact on sales of a healthcare product may present a challenge to search engine development.

A healthcare product manufacturer may obtain access to contents of the on-line discussions as an anonymous user with read access. A healthcare product manufacturer may also obtain access to contents of the on-line discussions as a sponsor of the on-line discussion forum. As a sponsor, the healthcare product manufacturer may also identify a registered user through the on-line registration database. Additionally, a healthcare product manufacturer may moderate the on-line discussion forum to facilitate discussions and even elicit more specific responses. For example, a manufacturer may host their own discussion boards or configure an automated agent (an Internet bot) to interface with other forums or boards.

Further, on-line discussions may be conducted by users of a mobile application 236. Example mobile applications for on-line discussions may include WeChat, Line, or Google Hangout, etc. The mobile application may be developed for any operating system including, for example, Windows, Android, iOS, etc. The mobile application may be developed using any existing or yet to be developed languages. Example languages include Java, C, C++, Python, etc. The mobile application may include a mobile application on an iPhone, an Android phone, a blackberry, an iPad, etc. The mobile application may enable a user to chime in the user's opinion or experience of an identifiable event just transpired. The contents of the discussion may be accessible at a server maintained at an on-line app store 106. A healthcare product manufacturer may be the sponsor of a mobile application and thus may have access to the server at the on-line app-store.

Additionally, on-line users may document their experience at a blogging site 238. In general, blogs tend to be more thorough and detailed than shorter forms of on-line postings. Blogs may also provide a chronicle of daily or hourly experiences as a user continues a usage course. These blogs may be traced to an individual user through the registered account. The contents of these blogs may be publicly viewable, i.e., the contents may be viewable to a larger audience either from within a social circle of the user or through a search engine. These blogs may contain opinions or experiences of the author, which may be based on the author's personal observation or the author's second-hand experience acquired from users other than the author.

When posting comments on-line, the application used by the consumer may publish the contents in a manner consistent with a semantic web standard. To facilitate information processing (such as, for example, search and comparison) by computing machines, the World Wide Web Consortium (W3C) has been developing a semantic web standard for on-line publications. Generally, such standard favors description of web page contents in the metadata that is readable by web crawlers and agents. Metadata generally refers to descriptive data embedded in the source code associated with a web publication but may not be viewable to a human reader through a browser, unless the user chooses to view the source code. Newly developed web publication languages may implement the strategy of incorporating at least portions of publication contents in the metadata. Example language formats may include Resource Description Framework (RDF) language, Web Ontology Language (OWL), and Extensible Markup Language (XML), all of which may serve as an improvement over Hyper Text Markup Language (HTML).

To search online media channels, a feed reader 240 may track one or more on-line communities. The tracking can be done in real-time through a feed reader as the comments are posted. The tracking can also be done in a batch after the on-line postings have reached a certain size or on an hourly or daily basis. Feed reader 240 may include meta search 242, feed aggregation 244, and content import 246, as described above.

Returning to the bucketing arrangement illustrated in FIG. 2B, activity level may be indicated by the number of results for a given event, or the number of individuals involved in the event. For example, a marathon event may have moderate exposure on social and online media, but include a large number of participants. Alternatively, a disaster may involve a small or large number of individuals and be heavily reported, such as the Boston bombing event, typhoon Haiyan in the Philippines, etc. A further example is a healthcare related policy change that might not receive much exposure, but affects a large population. Hence the trend identification process may factor in the nature and characterization of the underlying event to account for the activity level. In fact, the forecasting process may not be entirely based on a popularity vote, as in a democratic election.

Impact may refer to the effect caused by an identifiable event on the sales of healthcare product. Generally, some identifiable events may lead to an increase in the demand for a particular healthcare product under the circumstances. Other identifiable events may lead to a decrease in the demand for the particular healthcare product under the same circumstances. The impact may reflect the directional effect caused by the identifiable event. The impact of the identifiable event may be time-dependent to better characterize the directional effect on a particular healthcare product as time elapses after the identifiable event. The impact may also include numerical grades to quantify the magnitude of the effect on the particular healthcare product.

Returning to FIG. 2A, a database 212 of relationship between existing health indications and event may be established. The events may include identified events from logged search results as stored in log file 210. The database may be generated based on a correlation between events identified by the search results (as obtained in accordance with the discussions above) and historical sales or prescription data related to the event. The database will contain the synthesized event and/or social media illustrating a positive or negative trend in electronic conversations about a specific product, manufacturer, therapy or wholesaler but not limited to these encompassing the health care industry. The database may be maintained and updated based on recent feedback, for example, to incorporate newly identified indications, to incorporate feedback from a human operator to highlight a relationship between a healthcare indication and a momentum in sales activities. In some implementations, a causal link may exist between a healthcare indication and a healthcare product while a strong correlation may exist between a healthcare indication and an identifiable event (as illustrated in the log file). In some implementations, entries in database 212 may be established after statistical analysis, including, for example, regression analysis, student t-test, ANOVA analysis, to confirm a statistically significant relationship. The relationship between identifiable events to health indications (as well as healthcare products), for example, pain medication related to sporting events, may be updated in the database regularly to account for new events as the new events occur.

The database 212 may then be used to analyze the logged search results in log file 210 against historical sales and prescription based data 214. For example, search results in the log file 210 may be compared to the relationship information (stored in the database) between, for example, healthcare indication and historical event, as tabulated in database 212. From the health indication, for example, a class of drugs (or healthcare product including medical/healthcare products) may be identified based on the identity of a customer. Notably, the customer may include a manufacturer (e.g., pharmaceutical companies or medical device companies) or a provider (e.g., insurance providers) of the class of drugs (or healthcare product). Based on the predicted trending information, the customer may prepare its manufacturing or distribution activities accordingly.

Statistical forecasting engine 218 may analyze the identified results from the comparison between search results in log file 210 and historical relationship information in database 212. The analysis may include regression analysis, t-test analysis, ANOVA analysis, etc., to correlate the identified results against historical sales/prescription and over-the-counter data in an effort to project future sales for a customer. For example, a traditional regression analysis may identify a slope parameter and offset parameter for projecting sales of a healthcare product implicated by the comparison between search results in log file 210 and database 212. Based on commensurate weights assigned to the identified events, and the historical sales data, the slope parameter and offset parameter may be obtained. The updated slope parameter and offset parameter may extrapolate current sales data to project the upcoming sales data, in the absence of additional events (i.e., if nothing else is done or nothing else occurs). In some implementations, the statistical forecasting engine 218 may operate on existing data retrospectively to fine tune the database, or update the regression model, or to better understand the underlying driving forces that explain why and how a particular trending data occurred in the past.

The analysis may be performed automatically by a computing system. The computing system may include a distributed network of computers configured to analyze contents of the log file against the database according to load balancing tactics. The load balancing tactics may factor in the computing power of each computer system on the distributed network, the proximity of each computer system to the data being searched, the likelihood of hits when searching a particular portion of log file. As the world is increasingly and globally interconnected, log file may include aggregated comments posted by users from anywhere the world, the contents of which may be stored similarly anywhere in the world. Thus, the computing load may be distributed accordingly to improve efficiency, latency, and throughput. The analysis may employ any programming or scripting language capable of supporting text string search, including, but limited to, Practical Extracting and Reporting Language (PERL), python, Ruby, PHP Hypertext Preprocessor (PHP), SmallTalk, Java, C, C++, etc.

Results of the analysis may be graphically displayed to a human analyst on graphic display 216. In some implementations, results of the analysis 220 may be provided to customer in a text document. The analysis 220 may factor in information the customers 224 identifying the paying customer as well as the payment level (through subscription or pay-per-use). Customers 224 can include pharmaceutical companies with manufacturing capabilities, retail facilities in the distribution chain of a particular healthcare product, and consulting agencies charged to analyze data.

The analysis 220 may also factor in drug classification data 222 as additional data sources. Drug classification data 222 may also include class of trade (COT) data. COT data may define how pricing data are reported to the federal government, such as the federal drug administration (FDA), the drug enforcement agency (DEA), the center for disease control (CDC), the national instate of health (NIH), etc. COT data may also imply how a healthcare product is considered by federal regulators and how consumption of the healthcare product may be reimbursed or subsidized by the federal regulators. COT data may include business activity code (BAC) or business activity subcode (BASC), as defined by the DEA. COT may classify healthcare products as retail or specialty, as defined by government pricing organization (GPO). Such data can pertain to Group Purchasing Organizations (GPO) or their constituent members and drive internal grouping of profiles to project group impact. COT data may also factor in product/therapeutic area and distribution considerations.

The search weighted and bucketed results may be compiled to build a profile 226 of identified patterns effecting product movement and projecting future performance. Profile 226 may be delivered to customers via direct data feed, user interface, or via a customer consultant (to which the user interface is supplied). The profile may also be adjusted based on feedback from a human operator. The profile may additionally be adjusted based on an adaptive process of machine learning. Profiles may be tied to the product and may show sales trending data over a variable period compared with historical data, globally, or across a region. Data projected, if not for the occurrence of an event, can be displayed, as well as competitive data for the same health indication. The user interface can be configured to allow variations in, for example, the historical perspective or competitive comparison.

Figure 3A:
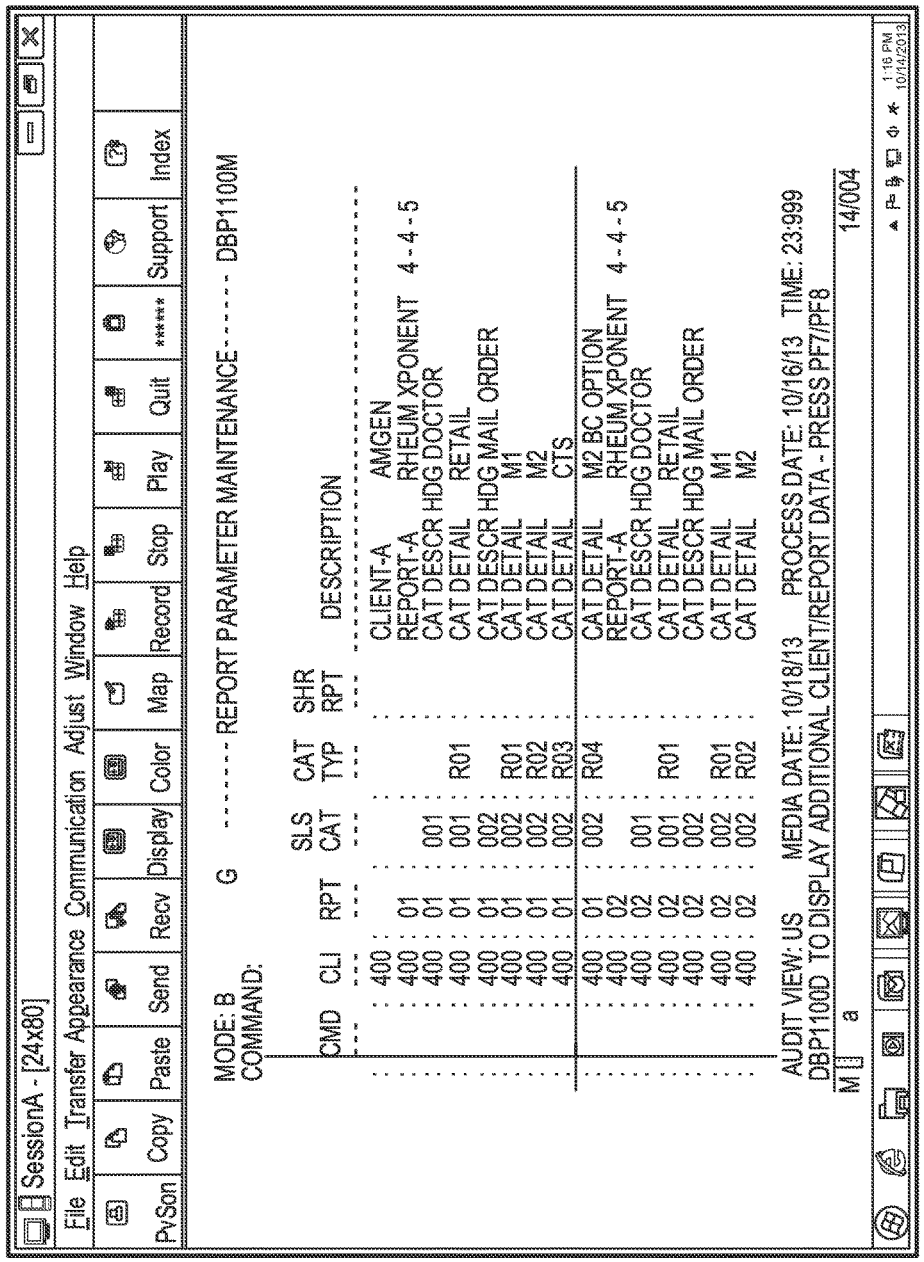
FIG. 3A is a screen shot showing report parameters for generating a profile according to some implementations
Figure 3B:
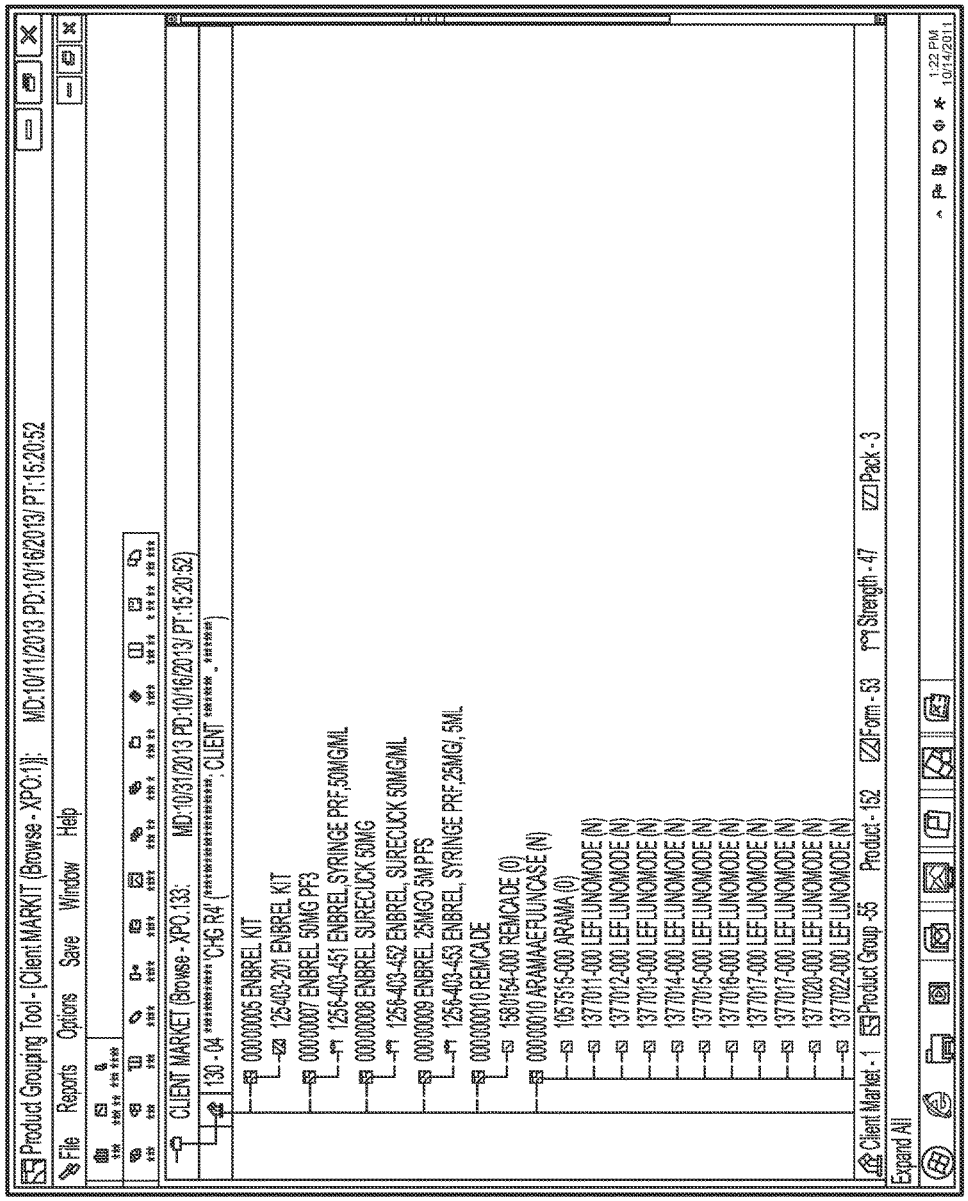
FIG. 3B is another screen shot showing product names to be searched for identifying trending data according to some implementations.

In some implementations, the search may include client (e.g., pharmaceutical manufacturer/wholesalers) specific searches by company name (full name or any form of abbreviation), by product name (Branded and Generic), or by market (defined within a USC). In some implementations, the search may utilize internal health care faculties input, for example, by chain name, by wholesaler name, by software vendor name, by Integrated Delivery Network (IDN) name, by GPO name, or by health system name. The IDN may refer to the network leveraged by a healthcare organization. In some searches, statistical methodologies may be incorporated, leading to, for example, more favored treatment of on-line communications posted by healthcare professionals (such as medical doctors) than private citizens (such as individual patients). In some searches, preference may be given by weighting on health care professionals over private citizens based on a person's title or identifiable profession FIG. 3A is a screen shot showing report parameters for generating a profile according to some implementations. Report parameters include search targets (at on-line communities) as will be reported to a client, for example, a pharmaceutical company. As illustrated, the search report parameters may include company name, product name, delivery option (mail order, retail, prescription by doctor, etc.). The search report parameters may be used in determining search criteria as well as defining the sales and/or prescription data bucket by client used in historical data graphing FIG. 3B is another screen shot showing product names to be searched for identifying trending data according to some implementations. As illustrated, product names to be searched include: Enbrel, Remicade, Leflunomide, methotrexate, Arava, etc. Notably, these are just some examples of applicable products.

FIG. 3C is yet another screen shot showing search criteria established according to some implementations. As illustrated, search criteria are established based on the product names shown in FIG. 3B.

Figure 3D:
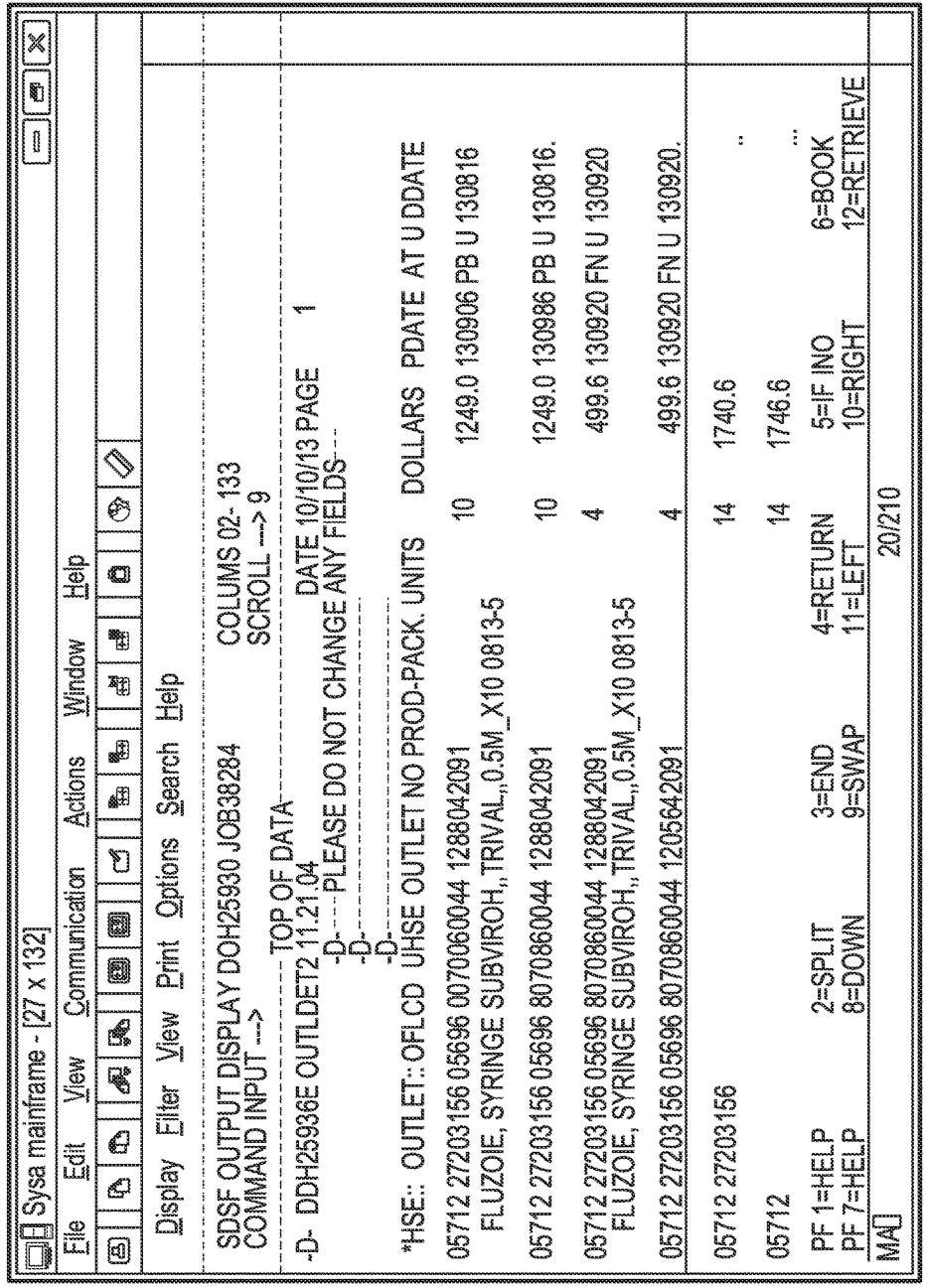
FIG. 3D is still another screen shot showing extracts from an example history file being used for identifying trending data according to some implementations.

FIG. 3D is still another screen shot showing extracts from an example history file being used for identifying trending data according to some implementations. As illustrated, the historical data shows a two-year movement (including date, duration, number of units, dollar amount, etc.) for a health care facility. Notably, the healthcare facility may generally refer to a GPO, a healthcare system (e.g., a hospital), and facilities within a healthcare system.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method, the method comprising:

text mining, according to an ontology, in a social media channel that is coupled to a search engine through a feed reader interface to identify at least one event for determining an impact to demand for at least one healthcare product, the social media channel collecting and posting inputs from user mobile devices;

determining, using a distributed computer network that is configured to access a data storage device, a healthcare indication based on analysis of a database that includes information encoding historical events, contemporaneous records data of healthcare products, and data representing causal links between the healthcare indication and the healthcare products in the database, wherein the healthcare indication represents a specific medical condition that necessitates treatment using the healthcare products;

determining, using the distributed computer network and based on analysis of each historical event, impact to demands for the healthcare products whose record data is encoded, each historical event being statistically correlated with the healthcare indication that is treatable using the healthcare products;

using the determined healthcare indication and impact to demands for the healthcare products, identifying a healthcare product that has a causal link to the healthcare indication based on data representations of the database, wherein the records data of the identified healthcare product is encoded by information accessed during analysis of the database;

correlating, using a statistical forecasting engine of the distributed computer network, the identified at least one event with records data of the identified healthcare product based on statistical analysis to:

(i) combine weights and number of occurrences of terms corresponding to the identified at least one event as identified from the social-media channel, both weights and number of occurrences tapering off as time elapses since the identified at least one event, and (ii) determine a trend for the identified healthcare product during a projected period since the identified at least one event;

comparing the determined trend for the identified healthcare product with actual data of the same identified healthcare product during the projected period when the actual data of the same identified healthcare product during the projected period becomes available in the database;

identifying a difference between the determined trend and the actual data of the same identified healthcare product during the projected period; and based on the identified difference, enhancing a trend projection capability of the statistical forecasting engine to reduce the identified difference between the determined trend and the actual data, wherein the trend projection capability is enhanced relative to a first projection capability of the statistical forecasting engine in response to the distributed computer network iteratively updating the database to account for new events that have a correlation to the healthcare indication and the identified healthcare product, and wherein enhancing the trend projection capability of the statistical forecasting engine includes:

executing a load balancing tactic for updating a regression model of the statistical forecasting engine, the load balancing, tactic being executed to balance a computing load distributed to each computer of the distributed computer network that updates the regression model;

wherein the load balancing tactic and the undated regression model are used to analyze the new events stored at the database in response to the iterative updates of the database.

2. The method of claim 1, further comprising:
performing a regression analysis on the records data to determine the trend for the identified healthcare product, the regression analysis accounting for contributions from the identified at least one event.

3. The method of claim 1, further comprising:
dynamically presenting the determined trend for the healthcare product against a competing healthcare product with identical healthcare indication in a graphic user interface such that the determined trend is projected in response to each of the at least one identified event.

4. The method of claim 1, further comprising:
providing the determined trend to cumulatively build a profile of the identified healthcare product.

5. The method of claim 4, further comprising:
recording actual data for the identified healthcare product in the profile; and
comparing the trend for the identified healthcare product in the profile to actual sales data.

6. The method of claim 1, further comprising:
receiving the ontology for the at least one healthcare product; and
refining the ontology by incorporating reporting parameters that include at least one of: product level data, supplier data, facility level data, or class of trade data.

7. The method of claim 1, further comprising:
receiving the ontology for the at least one healthcare product; and
refining the ontology by incorporating event-driven parameters defined to include at least one of: a natural event, or a government event.

8. A computer system, comprising at least one processor, wherein the at least one processor is configured to perform the operations of:
applying an ontology to text mine in a corresponding social-media channel where inputs from user mobile devices have been collected and posted such that at least one event is identified to determine an impact to demand for at least one healthcare product relating to a particular healthcare indication;

determining, using a distributed computer network that is configured to access a data storage device, a healthcare indication based on analysis of a database encoding information that includes historical events and data representing causal links between the healthcare indication and healthcare products in the database, the database being developed from historical events that are each statistically correlated with one or more healthcare indications, and wherein the healthcare indication represents a specific medical condition that necessitates treatment using the healthcare products; and determining, using the distributed computer network and based on analysis of each historical event, impact to demands for the healthcare products in the database;

using the determined healthcare indication and impact to demands for the healthcare products, identifying a healthcare product that has a causal link to the healthcare indication based on data representations of the database;

correlating, using a statistical forecasting engine of the distributed computer network, the identified at least one event with historical activities of the identified healthcare product based on statistical analysis to:

(i) combine weights and number of occurrences of terms corresponding to the identified at least one event as text mined from the social-media channel, both weights and number of occurrences tapering off as, time elapses since the identified at least one event, and (ii) determine a trend for the identified healthcare product during a projected period since the identified at least one event;

comparing the determined trend, for the identified healthcare product with actual data of the same identified healthcare product during the projected period;

identifying a difference between the determined trend and the actual data of the same identified healthcare product during the projected period; and based on the identified difference, enhancing a trend projection capability of the statistical forecasting engine to reduce the identified difference between the determined trend and the actual data, wherein the trend projection capability is enhanced relative to a first projection capability of the statistical forecasting engine in response to the distributed computer network iteratively updating the database to account for new events that have a correlation to the healthcare indication and the identified healthcare product, and wherein enhancing the trend projection capability of the statistical forecasting engine includes:

executing a load balancing tactic for updating a regression model of the statistical forecasting engine, the load balancing, tactic being executed to balance a computing load distributed to each computer of the distributed computer network that updates the regression model;

wherein the load balancing tactic and the undated regression model are used to analyze the new events stored at the database in response to the iterative updates of the database.

9. The computer system of claim 8, further comprising:
performing a regression analysis on the historical activities to determine the trend for the identified healthcare product, the regression analysis accounting for contributions from the identified at least one event.

10. The computer system of claim 8, wherein the operations further comprise:
   dynamically presenting the determined trend for the healthcare product against a competing healthcare product with identical healthcare indication in a graphic user interface such that the determined trend is projected in response to each of the at least one identified event.

11. The computer system of claim 8, wherein the operations further comprise:
   providing the determined trend, to cumulatively build a profile of the identified healthcare product.

12. The computer system of claim 8, wherein the operations further comprise:
   receiving the ontology for the at least one healthcare product; and
   refining the ontology by incorporating reporting parameters that include at least one of: product level data, supplier data, facility level data, or class of trade data.

13. The computer system of claim 8, wherein the operations further comprise:
   receiving the ontology for the at least one healthcare product; and
   refining the ontology by incorporating event-driven parameters defined to include at least one of: a natural event, or a government event.

14. A non-transitory computer-readable medium comprising software instructions that, when executed by a computer, causes the computer to perform the operations of:
   applying an ontology to text mine in a corresponding social-media channel where inputs from user mobile devices have been collected and posted such that at least one event is identified to determine an impact to demand for at least one healthcare product relating to a particular healthcare indication;
   determining, using a distributed computer network that is configured to access a data storage device, a healthcare indication based on analysis of a database encoding information that includes, historical events and data representing causal links between the healthcare indication and healthcare products in the database, the database being developed from historical events that are each statistically correlated with one or more healthcare indications, and wherein the healthcare indication represents a specific medical condition that necessitates treatment using the healthcare products; and
   determining, using the distributed computer network and, based on analysis of each historical event, impact to demands for the healthcare products in the database;
   using the determined healthcare indication and impact to demands for the healthcare products, identifying a healthcare product that has a causal link to the healthcare indication based on data representations of the database;
   correlating, using a statistical forecasting engine of the distributed computer network, the identified at least one event with historical activities of the identified healthcare product based on statistical analysis to:
   (i) combine weights and number of occurrences of terms corresponding to the identified at least one event as text mined from the social-media channel, both weights and number of occurrences tapering off as time elapses since the identified at least one event, and
   (ii) determine a trend for the identified, healthcare product during a projected period since the identified at least one event;
   comparing the determined trend for the identified healthcare product with actual data of the same identified healthcare product during the projected period;
   identifying a difference between the determined trend and the actual data of the same identified healthcare product during the projected period; and
   based on the identified difference, enhancing a trend projection capability of the statistical forecasting engine to reduce the identified difference between the determined trend and the actual data, wherein the trend projection capability is enhanced relative to a first projection capability of the statistical forecasting engine in response to the distributed computer network, iteratively updating the database to account for new events that have a correlation to the healthcare indication and the identified healthcare product, and wherein enhancing the trend projection capability of the statistical forecasting engine includes:
   executing a load balancing tactic for updating a regression model of the statistical forecasting engine, the load balancing, tactic being executed to balance a computing load distributed to each computer of the distributed computer network that updates the regression model;
   wherein the load balancing tactic and the undated regression model are used to analyze the new events stored at the database in response to the iterative updates of the database.

15. The method of claim 1, wherein enhancing the trend projection capability of the statistical forecasting, engine further includes:
   executing, at the distributed computer network, the load balancing tactic to analyze data in a log file against the database, the data in the log file comprising information about recent events obtained from search results of the search engine; and
   in response to executing the load balancing tactic, iteratively updating, using the computers of the distributed computer network, the database to account for the new events that have the correlation to the healthcare indication and the identified healthcare product.

16. The method of claim 15, wherein executing the load balancing tactic comprises:
   obtaining a computing power for each computer in the distributed computer network;
   determining a geographic location of the data in the log file and a proximity of the data to one or more computers of the distributed computer network; and
   distributing a computing load for iteratively updating the database using the obtained computing power and the proximity of the data to the one or more computers.

17. The computer system of claim 8, wherein enhancing the trend projection capability of the statistical forecasting engine further includes:
   executing, at the distributed computer network, the load balancing tactic to analyze data in a log file against the database, the data in the log file comprising information about recent events obtained from the social-media channel; and
   in response to executing the load balancing tactic, iteratively updating, using the computers of the distributed computer network, the database to account for the new events that have the correlation to the healthcare indication and the identified healthcare product.

18. The computer system of claim 17, wherein executing the load balancing tactic comprises:
  obtaining a computing power for each computer in the distributed computer network;
  determining a geographic location of the data in the log file and a proximity, of the data to one or more computers of the distributed computer network; and
  distributing a computing load for iteratively updating the database using the obtained computing power and the proximity of the data to the one or more computers.

19. The non-transitory computer-readable medium of claim 14, wherein enhancing the trend projection capability of the statistical forecasting engine further includes:
  executing, at the distributed computer network, the load balancing tactic to analyze data in a log file against the database, the data in the log file comprising information about recent events obtained from the social-media channel; and
  in response to executing the load balancing tactic, iteratively updating, using the computers of the distributed computer network, the database to account for the new events that have the correlation to the healthcare indication and the identified healthcare product.

20. The non-transitory computer-readable medium of claim 19, wherein executing the load balancing tactic comprises:
  obtaining a computing power for each computer in the distributed computer network;
  determining, a geographic location of the data in the log file and a proximity of the data to one or more computers of the distributed computer network; and
  distributing a computing load for iteratively updating the database using the obtained computing power and the proximity of the data to the one or more computers.

* * * * *

UNITED STATES PATENT AND TRADEMARK OFFICE
CERTIFICATE OF CORRECTION

PATENT NO. : 10,296,927 B2  
APPLICATION NO. : 14/136706  
DATED : May 21, 2019  
INVENTOR(S) : Soria et al.

Page 1 of 1

It is certified that error appears in the above-identified patent and that said Letters Patent is hereby corrected as shown below:

In the Drawings

Figure 1A, Sheet 1 of 9, in Component "102", replace "Articales" with "Articles"

In the Specification

Column 2, Line 6, after "a" and before "computer system", delete repetitive word "computer system"

Column 6, Line 10, after "reporting" and before "parameters", insert --data--

In the Claims

Column 20, Claim 8, Line 57, after "balancing" and before "tactic", delete "--,--"

Column 22, Claim 14, Line 24, after "balancing" and before "tactic", delete "--,--"

Column 22, Claim 15, Line 2, after "forecasting" and before "engine", delete "--,--"

Signed and Sealed this  
Sixth Day of August, 2019

Andrei Iancu  
*Director of the United States Patent and Trademark Office*